United States Patent [19]
Kohlpaintner et al.

[11] Patent Number: 5,817,775
[45] Date of Patent: Oct. 6, 1998

[54] PHOSPHINES AND CATALYSTS CONTAINING THE SAME

[75] Inventors: Christian W. Kohlpaintner, Oberhausen, Germany; Brian E. Hanson; Hao Ding, both of Blacksburg, Va.

[73] Assignees: Celanese International Corporation, Dallas, Tex.; Virginia Polytechnic Ins., Blacksburg, Va.

[21] Appl. No.: 731,232

[22] Filed: Oct. 10, 1996

[51] Int. Cl.⁶ ........................................................ C07F 13/00
[52] U.S. Cl. .................................. 534/14; 534/10; 556/13
[58] Field of Search .................................. 556/13, 15, 16, 556/19, 20, 21; 568/13, 17; 534/10, 14

[56] References Cited

U.S. PATENT DOCUMENTS

| | | | |
|---|---|---|---|
| 4,668,809 | 5/1987 | Oswald et al. | 556/18 |
| 4,668,823 | 5/1987 | Murray | 568/17 |
| 4,668,824 | 5/1987 | Jenck et al. | 568/15 |
| 4,673,753 | 6/1987 | Siedle | 556/15 |
| 4,835,202 | 5/1989 | Pastor et al. | 524/154 |
| 5,057,618 | 10/1991 | Herrmann et al. | 556/21 |
| 5,274,183 | 12/1993 | Herrmann et al. | 562/35 |
| 5,306,835 | 4/1994 | Sato et al. | 556/16 |
| 5,631,393 | 5/1997 | Kohlpaintner et al. | 556/17 |

OTHER PUBLICATIONS

Harson et al., *NATO ASI Ser.*, Ser. 3,5 (Aqueous Organometallic Chemistry and Catalysis), pp. 149–158, 1995 month unavailable.

Ding et al., *J. Chem. Soc., Chem. Commun.*, (24), pp. 2747–2748, 1994 month unavailable.

Ding et al., *Inorg. Chim. Acta.*, 229 (1–2), pp. 329–333, 1995 month unavailable.

Ding et al., *Organometallics*, 13(10), pp. 3761–3763, 1994 month unavailable.

Ding et al., *Angew. Chem. Int. Ed. Engl.*, 34(15), pp. 1645–1647, 1995 month unavailable.

*Primary Examiner*—John Kight
*Assistant Examiner*—Dameron Jones
*Attorney, Agent, or Firm*—James J. Mullen

[57] ABSTRACT

The present invention provides novel a phosphine as a ligand (L) and having the formula

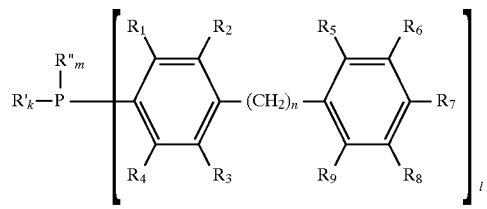

wherein k, l, m, R', R", $R_1$-$R_9$ and n are defined herein, and which can be complexed with a transition metal (M') and an auxiliary ligand Y to form a novel catalyst having the formula M'$L_x$$Y_z$ useful in such applications as hydroformylation.

6 Claims, 1 Drawing Sheet

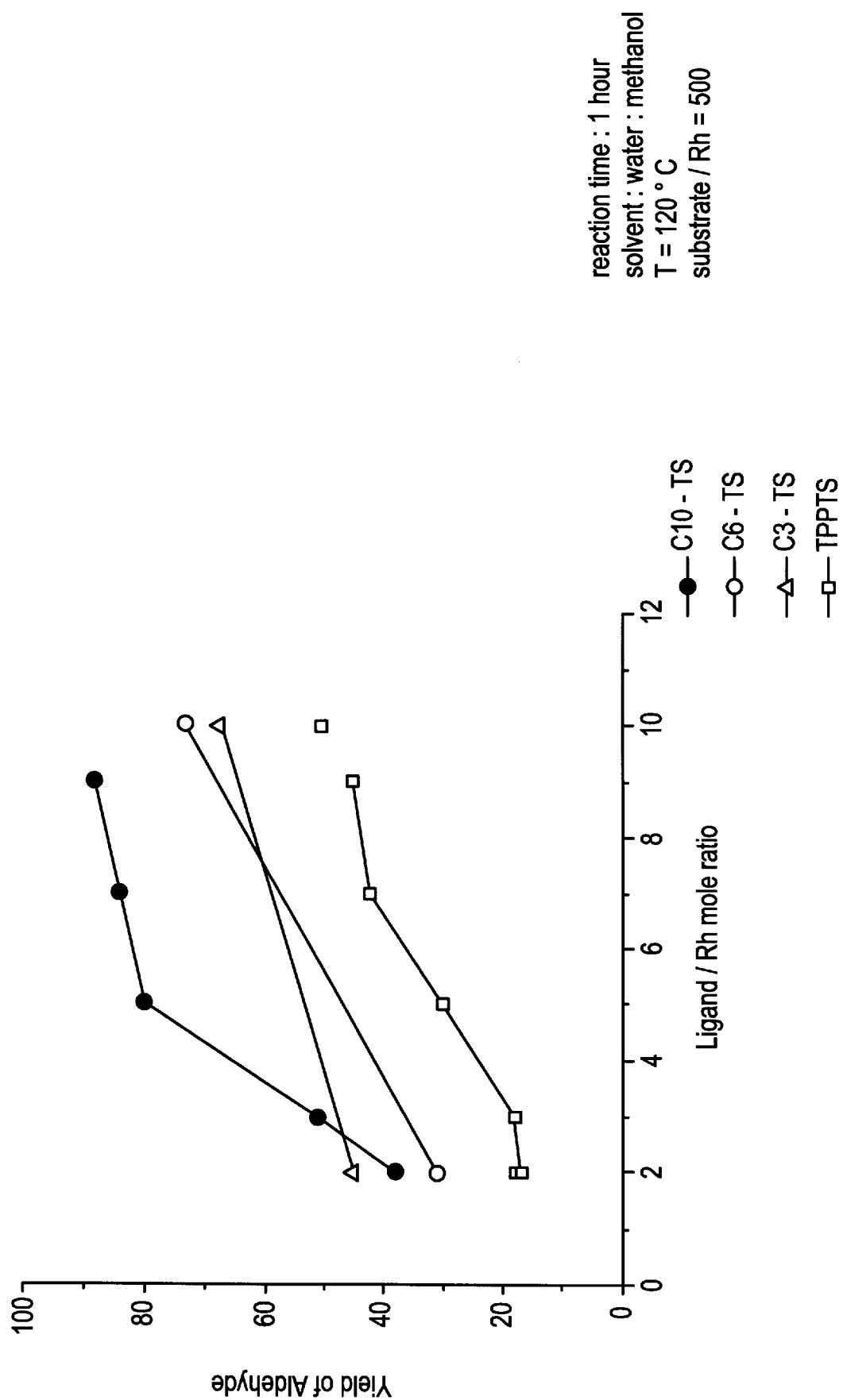

PHOSPHINES AND CATALYSTS CONTAINING THE SAME

BACKGROUND OF THE INVENTION

1. Field of the Invention

The present invention is directed to novel water-soluble sulfonated phosphines, catalysts containing the same, processes for preparing such phosphines and catalysts, and processes for using such catalysts.

2. General Background & Prior Art Problems

One of the major problems of homogeneous catalysis is the separation of catalyst from product. The lifetime of a catalyst in an industrial process is greatly affected by the means of separation. It has been shown that a two-phase system with water-soluble phosphines as ligands can be very effective to achieve easy recycling of catalysts. However, the reactivity of the water-soluble catalyst is somewhat limited by the solubility of the organic substrate in aqueous phase. The synthesis of water-soluble phosphines has reached a stage that it is now possible to tailor the structure of a phosphine for improved reactivity while retaining excellent water solubility for good catalyst separation.

A widely used method for synthesizing water-soluble phosphines is direct sulfonation to introduce one or more sulfonate groups onto a phenyl ring bonded to phosphorus. Unfortunately, the direct sulfonation often requires harsh conditions and long reaction times. The reaction produces a significant amount of phosphine oxide along with phosphines with different degrees of sulfonation. All these complicate the purification of the sulfonated products and contribute to a poor yield of sulfonation products. Therefore, the conventional direct sulfonation is not very suitable for chiral and non-chiral water-soluble phosphine synthesis since a large portion of expensive chiral phosphine is going to be sacrificed in direct sulfonation. For this reason perhaps, the yields for the direct sulfonation of chiral phosphines such as BDPP and BINAP are not reported.

One of the most interesting chiral biphosphines is (R)-(+)- and (S)-(-)-2,2'-bis (diphenylphosphino)-1,1'-binaphthyl (BINAP). It shows exceptional enantioselectivity for asymmetric hydrogenations. The direct sulfonation of BINAP results in a mixture of phosphines with various degrees of sulfonation. The uncertainty of the sulfonated sites causes difficulties for characterization of the ligand and its metal complexes.

Thus, there is a need for new compounds which are water-soluble, exhibit outstanding surface active properties in two-phase catalysis, particularly in the area of two phase hydroformylation of olefins such as 1-octene, and are easily accessible by mild sulfonation conditions.

3. Description of the Prior Art

The following prior art references are disclosed for informational purposes.

U.S. Pat. No. 5,057,618 discloses complex compounds containing sulfonated phenyl phosphines.

U.S. Pat. No. 5,274,183 discloses water-soluble sulfonated diphosphines.

Organometallics 1994, 13, 3761–3763 discloses the preparation of sulfonated tertiary phosphines.

Other references pertinent to phosphine ligands, processes for preparing the same, and catalysts containing the same include:

1. W. A. Herrmann; C. W. Kohlpaintner, *Angew. Chem. Int. Ed. Engl.*, 1993, 32, 1524–1544.
2. R. Noyori, *Chem. Soc. Rev.*, 1989, 18, 187.
3. R. Noyori; M. Kilamura, *Modem Synthetic Methods*, Vol. 5, R. Scheffold ed., Berlin: Springer-Verlag, 1989, 115–198.
4. R. Noyori, *Chemtech*, Jun. 1992, 360–367.
5. Y. Amranni; L. Lecomte; D. Sinou; J. Bakos; I. Toth; B. Heil, *Organometallics*, 1989, 8, 542–547.
6. K. Wan; M. E. Davis, *J. C. S., Chem. Commun.*, 1993, 1263.
7. H. Ding; B. E. Hanson; T. Bartik; B. Bartik, *Organometallics*, 1994, 13, 3761.
8. H. Ding; B. E. Hanson, *Angew. Chem. Int. Ed. Engl.*, 107, 1728 (1995).
9. A. S. C. Chan, *Chemtech*, Mar. 1993, 47–51.
10. N. Sayo; H. Kumobayashi; S. A. Kutagawa; R. Noyori; H. Takaya, EP-A-0 295 890 (19 6 1987).
11. W. S. Knowles, *Acc. Chem. Res.*, 1983, 16, 106.
12. W. S. Knowles; W. O. Christopher; K. E. Koening; C. F. Hobbs, *Adv. Chem. Ser.*, 1982, 196, 325.
13. T. Ohta; H. Takaya; M. Kitamura; K. Nagai; R. Noyori, *J. Org. Chem.*, 1987, 52, 3174.
14. M. Fiorini; G. M. Giongo, *J. Mol. Catal.*, 1979, 5, 303.
15. M. Fiorini; G. M. Giongo, *ibid*, 1980, 7, 411.
16. J. E. Babin; G. T. Whiteker, World Patent. WO 93/03839, 1993.
17. H. Ding; B. E. Hanson, *J. C. S., Chem. Commun.*, 1994, 2747.
18. M. Vondenhof; J. Mattay, *Tetrahedron Lett.*, 1990, 31, 985.
19. *J Org. Chem.*, D. Cai; J. F. Payack; D. R. Bender; D. L. Hughes; T. R. Verhoeven; P. J. Reider, 1994, 59, 7180.
20. T. Maninaran; T-C. Wu; W. D. Klobucar; C. H. Kolich; G. P. Stahly; F. R. Fronczek; S. E. Watkins, Organometallics, 1993, 12, 1467.
21. K. Wan; M. E. Davis, J Catal., 1994, 148, 1.
22. D. Cai; J. F. Payack; D. R. Bender; D. L. Haghes; T. R. Verhoeven; P. J. Reider, *J. Org. Chem.*, 1994, 59, 7180.

All of the above cited prior art and any other references mentioned herein are incorporated herein by reference in their entirety.

SUMMARY OF THE INVENTION

The present invention provides novel phosphine ligands having the formula

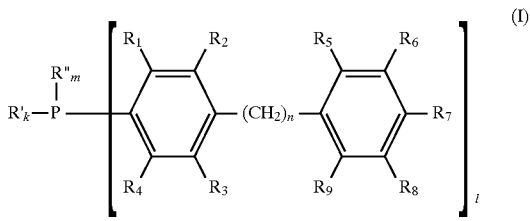

wherein $R_1$-$R_9R'$, $R''$, k, l, m, and n are defined herein, and which can be complexed with a transition metal and an auxiliary ligand to form a novel catalyst useful in such applications as hydroformylation.

DETAILED DESCRIPTION OF THE INVENTION

The present invention provides, in part, a novel phosphine having the formula

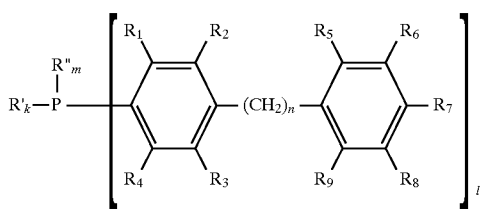

wherein:
(i) k+l+m=3, and k and m are each separately 0, 1, or 2, and l is 1, 2, or 3
(ii) R' and R" may be the same or different and may be chiral or non-chiral
(iii) R' and R" are each independently selected from the group consisting of an optionally substituted aliphatic group and an optionally substituted aryl group, for example, R' and R' are each independently selected from the group consisting of
  (a) straight or branched chain alkyl $C_1$—$C_{20}$,
  (b) cycloalkyl $C_1$—$C_{20}$,
  (c) alkoxy $C_1$—$C_{20}$,
  (d) substituted or unsubstituted phenyl, naphyl or anthryl, and
  (e) aryloxy.
(iv) $R_1$–$R_9$ are each independently selected from the group consisting of
  (a) hydrogen,
  (b) halogen,
  (c) —$SO_3M$ where M is any suitable cation, e.g. a cation selected from the group consisting of alkali metal, alkaline earth metals, and $N(R)_4^\oplus$ where R is selected from the group consisting of H, alkyl $C_1$—$C_{20}$ and phenyl,
  (d) alkyl $C_1$—$C_{20}$,
  (e) —$CO_2M$ where M is the same as defined in (c),
  (f) —$N^\oplus(R)_3 X^\ominus$ where $X^\ominus$ is a halide and R is the same as defined in (c),
  (g) —CN,
  (h) —OR where R is the same as defined in (c),
  (i) —C(O)—OR where R is the same as defined in (c),
  (j) —$P(R)_2$ where R is the same as defined in (c), and
(v) n is an integer which is 1 to 16 where l is 1 or 2, but n is 9 to 16 when l is 3, In order to provide the greatest water solubility, at least one of $R_1$ to $R_9$ is —$SO_3M$ where M is any suitable cation such as an alkali metal (e.g. Na, K, Li, Rb, Cs), alkaline earth metals such as Mg, and Ca, and $N(R)_4$ where R is H, alkyl $C_1$—$C_{20}$ or phenyl.

In the above definitions of $R_1$–$R_9$, the term "halogen" includes chlorine, fluorine, bromine, and iodine. The term "alkyl" includes straight and branch chained, saturated hydrocarbon radicals having from 1 to 20 carbon atoms such as, for example, methyl; ethyl; 1-methylethyl; 1,1,-dimethylethyl; propyl; 2-methylpropyl; butyl; pentyl; hexyl, and the like.

A preferred phospine has the formula

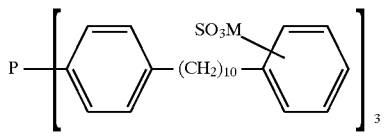

wherein M is an alkali metal.

In another facet of the present invention, the phosphines (ligands) of Formula I are complexed with a transition metal (M') and an auxiliary ligand to yield new catalysts having the formula:

$$M'L_xY_z \qquad (III)$$

wherein:
(A) M' is a transition metal
(B) L is the ligand of formula I above
(C) Y is an auxiliary ligand and selected from the group consisting of CO, CN, RCN, R, halogen, H, C(O)R, C(O)OR, NHR, $N(R)_2$, O, bipyridine, OR, SR, and S, where R is $C_1$—$C_8$, and
(D) x+z is an integer having a value of 2–9.

In Formula III, M' is any metal or transition metal which can be complexed with L (Formula I), i.e., bound to the phosphorus atom. M' is selected from the group consisting of chromium, manganese, iron, cobalt, nickel, copper, molybdenum, technetium, ruthenium, rhodium, palladium, silver, cadmium, tungsten, rhenium, osmium, indium, platinum, gold, and mercury. Such metal is from the groups IB, VII, A, and VIII A of the Periodic Table (IuPAC version numbers group 1 to 18).

In Formula III, x+z will vary depending upon the process it is used in as a catalyst. For example, in hydroformylation, Y may be CO and z is 1, i.e. there is usually at least one CO molecule along with the phosphine molecule and which are both directly bonded to a transition metal such as an Rh atom.

In Formula III, and when used in a hydroformylation process, the L/M' ratio is from about 2 to about 20; good results are achieved when this ratio is from about 6 to 12.

An example of a novel catalyst falling within formula III is the compound having the formula:

$$HM'(L)_w(CO)_{4-w} \qquad (IV)$$

wherein:
(a) M' is a transition metal
(b) L is a ligand of formula I
(c) w is an integer which is 1–4, and
(d) CO is an auxiliary ligand "Y" defined above.

In general, the novel phosphine ligands are prepared by a process which comprises the steps of (a) subjecting a dihalogenated alkane (straight chain where n is 9 to 16) to phenylation conditions by reacting it with a phenyl lithium compound, (b) the product of step (a) is treated with a mixed halogenated benzene material to produce a halogenated biphenyl substituted alkane, and (c) said biphenyl substituted alkane is then first reacted with lithium and then $PCl_3$ to yield the novel phosphine of the present invention. The temperatures and pressures in these steps are not critical, however, the temperature range is from about 0° C. to about 100° C. or greater. The pressure can be subatmospheric, atmospheric, or superatmospheric. The reaction times are not critical.

In order to provide the phosphine with water-soluble characteristics, the phosphine of Formula I, without the —$SO_3M$ group, is subjected to acid sulfonation and base conditions as shown below:

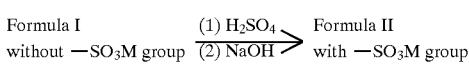

The acid, such as $H_2SO_4$, provides the —$SO_3^\ominus$ groups and the base, such as NaOH, providing metal M, such as sodium. In this fashion, it has unexpectedly been found that the sulfonation can be carried out in an easy manner (i.e., without significant oxidation or degradation reactions at very mild conditions), as compared to the prior art, and that the end result is a water-soluble phosphine which can be used (along with a metal for complexing to form a catalyst) in numerous organic processes. The temperatures, pressures and reaction times of this sulfonation are not critical.

It is to be understood that the processes as described above can employ a solvent to facilitate the reaction mechanism. Such solvents are, in general, organic and include, without limitation, THF, $Et_2O$, alkanes and/or mixtures thereof The novel catalysts sometimes referred to as a "metal-ligand complex catalysts" of the present invention are prepared either in situ or by reacting the water-soluble phosphine ligand with, for example, $Rh(CO)_2$ acac (acac= acetylacetonate) in an organic liquid/solvent such as methanol.

The term "complex" as used herein means a coordination compound formed by the union of one or more electronically rich molecules or atoms capable of independent existence with one or more electronically poor molecules or atoms, each of which is also capable of independent existence. The novel ligands, as indicated above, possess an element, i.e., phosphorus which has one available or unshared pair of electrons. When such elements have this electronic configuration it is capable of forming a coordinate bond with an atom such as rhodium.

Although the novel catalysts have a wide variety of applications and uses in numerous organic processes, one facet of the present invention relates to asymmetric synthesis in which, e.g. a prochiral or chiral compound is reacted in the presence of the optically active, metal-ligand complex catalyst which has at least one chiral center therein, in enantiomerically active form, to produce an optically active product.

Specifically, it has been unexpectedly found that the novel catalysts which have at least one chiral center therein, disclosed in the earlier part of this specification, can effect asymmetric synthesis in various processes with various substrates to produce a material which is optically active.

Thus where the ligand-metal complex has at least one chiral center, asymmetric synthesis can be carried out as described below.

The asymmetric synthesis processes of this invention are useful for the production of numerous optically active compounds, e.g., aziridines, cyclopropanes, aldehydes, alcohols, ethers, esters, amines, amides, carboxylic acids and the like, which have a wide variety of applications.

This part of the subject invention encompasses the carrying out of any known conventional synthesis in an asymmetric fashion with the novel optically active metal-ligand complex catalyst as disclosed herein. Some processes of this invention stereoselectively produce an enantiomer.

The permissible achiral, prochiral or chiral starting material reactants encompassed by part of the processes of this invention are, of course, chosen depending on the particular synthesis desired. Such starting materials are well known in the art and can be used in conventional amounts in accordance with conventional methods. Illustrative starting material reactants include, for example, substituted and unsubstituted aldehydes (intramolecular hydroacylation, aldol condensation), prochiral olefins (hydroformylation, hydrogenation, hydrocyanation, hydrosilylation, aziridination, hydroamidation, aminolysis, cyclopropanation, hydroboration, Diels-Alder reaction, codimerization), ketones (hydrogenation, hydrosilylation, aldol condensation, transfer hydrogenation, allylic alkylation), epoxides (hydrocyanation, nucleophilic ring opening reaction), alcohols (carbonylation) acyl and aryl chlorides (decarbonylation), a chiral Grignard reagent (Grignard cross coupling) and the like.

The novel catalysts of the present invention thus have utility in a wide variety of chemical processes, and particularly, in asymmetric synthesis reaction which include, without limitation; hydroxylation; cyclopropanation; aziridination; Diels-Alder reactions; cycloaddition, Michael addition; Aldol reaction; hydroboration; olefin and ketone hydrosilylation; hydrocyanation; addition of Grignards or organometallics to aldehydes and ketones; allylic alkylation; Grignard cross coupling; kinetic resolution; hydroamidation; olefin isomerization; aminolysis; hydrogenation; hydroformylation; and hydrocarboxylation.

The amount of catalyst in the reaction medium of a given process of this invention need only be that minimum amount necessary to catalyze the particular organic syntheses process desired. In general, concentrations in the range of from about 1 ppm to about 10,000 ppm, based on the starting reactant, should be sufficient for most syntheses processes. For example, in the catalyzed processes of this; invention, it is generally preferred to employ from about 10 to 1000 ppm and more preferably from 25 to 750 ppm.

The process conditions employable in the organic processes of this invention are, of course, chosen depending on the particular organic syntheses desired. Such process conditions are well known in the art. All of the organic syntheses processes of this invention can be carried out in accordance with the conventional procedures known in the art. Illustrative reaction conditions for conducting the asymmetric syntheses processes of this invention are described, for example, in Bosnich, B., Asymmetric Catalysis, Martinus Nijhoff Publishers, 1986 and Morrison, James D., Asymmetric Synthesis, Vol. 5, Chiral Catalysis, Academic Press, Inc., 1985, both of which are incorporated herein by reference in their entirety. Depending on the particular process, operating temperatures can range from about −80° C. or less to about 500° C. or greater and operating pressures can range from about 1 psia or less to about 10,000 psia or greater.

The reaction conditions of effecting, for example, the processes of this invention may be those heretofore conventionally used and may comprise a reaction temperature of from about −25° C. or lower to about 200° C. or higher and pressures ranging from about 1 to about 10,000 psia. Moreover, while such other syntheses may be performed under their usual conditions, in general, it is believed that they may be performed at lower temperatures than normally preferred due to the presence of the metal-ligand complex catalysts.

In general, the processes of this invention may be conducted at a reaction temperature from about −25° C. or lower to about 200° C. The preferred reaction temperature employed in a given process will, of course, be dependent upon the particular starting material and metal-ligand complex catalyst employed as well as the efficiency desired.

The processes are conducted for a period of time sufficient to produce the desired products. The exact time employed is dependent, in part, upon factors such as temperature, nature, and proportion of starting materials, and the like. The reaction time will normally be within the range of from about one-half to about 200 hours or more, and preferably from less than about 1 to 10 hours.

The processes of this invention may be conducted in the presence of an organic solvent for the metal-ligand complex catalyst. Depending on the particular catalyst and reactants employed, suitable organic solvents include, for example, alcohols, alkanes, alkenes, alkenes, ethers, aldehydes, ketones, esters, acids, amides, amines, aromatics, and the like. Any suitable solvent which does not unduly adversely interfere with the syntheses process can be employed and such solvents may include those heretofore commonly employed in known metal catalyzed processes. Increasing the dielectric constant or polarity of a solvent may generally tend to favor increased reaction rates.

Mixtures of one or more different solvents may be employed if desired. It is obvious that the amount of solvent is not critical to the subject invention and need only be that amount sufficient to provide the reaction medium with the particular metal concentration desired for a given process. In general, the amount of solvent when employed may range from about 5% by weight up to about 95% by weight or more, based on the total weight of the reaction medium.

The processes of this invention can provide optically active products by having very high enantioselectivity and regioselectivity. Enantiomeric excesses of preferably greater than 50% can be obtained by the processes of this invention. The processes of this invention can also be carried out at highly desirable reaction rates suitable for commercial use.

The desired products may be recovered in most cases by phase separation. Other separation methods include solvent extraction, crystallization, distillation, vaporization, wiped film evaporation, falling film evaporation, and the like. It may be desired to remove the products from the reaction systems as they are formed through the use of trapping agents as described in WO patent 88/08835.

The optically active products produced by the asymmetric syntheses processes of this invention can undergo further reaction(s) to afford desired derivatives thereof Such permissible derivitization reactions can be carried out in accordance with conventional procedures known in the art. Illustrative derivitization reactions include, for example, esterification, oxidation of alcohols to aldehydes, N-alkylation of amides, addition of aldehydes to amides, nitrile reduction, acylation of ketones by esters, acylation of amines, and the like.

Illustrative of suitable reactants in effecting the processes of this invention include by way of example:
AL alcohols
PH phenols
THP thiophenols
MER mercaptans
AMN amines
AMD amides
ET ethers
EP epoxides
ES esters
H hydrogen
CO carbon monoxide
HCN hydrogen cyanide
HS hydrosilane
W water
GR grignard reagent
AH acyl halide
UR ureas
OS oxalates
CN carbamates
CNA carbamic acids
CM carbonates
CMA carbonic acids
CA carboxylic acids
ANH anhydrides
KET ketones
OLE olefins
ACE acetylenes
HAL halides
SUL sulfonates
ALD aldehydes
NIT nitriles
HC hydrocarbons
DZ diazo compounds
BOR boranes
ESE enol silyl ethers
SUD sulfides Illustrative of suitable products prepared by the asymmetric syntheses processes of this invention include by way of example:
AL alcohols
PH phenols
THP thiophenols
MER mercaptans
AMN amines
AMD amides
ET ethers
ES esters
H hydrogen
CO carbon monoxide
SI silanes
UR ureas
OX oxalates
CN carbamates
CNA carbarmic acids
CM carbonates
CMA carbonic acids
CA carboxylic acids
ANH anhydrides
KET ketones
OLE olefins
ACE acetylenes
HAL halides
ALD aldehydes
NIT nitriles
HC hydrocarbons
CYP cyclopropanes
ABR alkylboranes
ADL aldols
AZ aziridines Illustrative of reactions encompassed within the scope of this invention include, for example, the following reactant/product combinations:

| REACTANT(S) | PRODUCT(S) |
| --- | --- |
| OLE, CO, H | ALD |
| OLE, CO, H | CA |
| ALD | KET |
| OLE, ALD | KET |
| OLE, HC | HC |
| OLE, CO | CA |
| OLE, CO, AMN | AMD |
| OLE | AZ |
| OLE, CO, AL | ES |
| KET, H | AL |
| EP, H | AL |
| OLE, AMN | AMN |
| OLE, AL | ET |
| AL, CO | CA |
| AL | ALD |
| OLE, HCN | NIT |
| OLE, HS | SI |
| OLE, CO, W | CA |
| OLE | OLE |
| GR | HC |
| AH | HAL |
| OLE, H | HC |
| OLE, BOR | AL |

-continued

| REACTANT(S) | PRODUCT(S) |
|---|---|
| OLE, BOR | ABR |
| OLE, DZ | CYP |
| KET, AL | AL |
| ALD, ESE | ADL |
| KET, ESE | ADL |
| KET, HS | AL |
| EP, CO, H | ALD |
| EP, HCN | NIT |
| ALD | CA |

As indicated above, the processes of this invention can be conducted in a batch or continuous fashion, with recycle of unconsumed starting materials if required. The reaction can be conducted in a single reaction zone or in a plurality of reaction zones, in series, or in parallel, or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Finally, the products of the process of this invention have a wide range of utility that is well known and documented in the prior art, e.g. they are especially useful as intermediates for pharmaceuticals, flavors, fragrances, agricultural chemicals, and the like. Illustrative therapeutic applications include, for example, non-steroidal anti-inflammatory drugs, ACE inhibitors, beta-blockers, analgesics, bronchodilators, spasmolytics, antihistamines, antibiotics, antitumor agents, and the like. For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The following specific examples are supplied for the purpose of better illustrating the invention. These examples are not intended, however, to limit or restrict the scope of the invention in any way and :should not be construed as providing conditions, parameters, or values which must be utilized exclusively in order to practice the present invention.

EXAMPLES (GENERAL)

All reactions and measurements were carried out using standard Schlenk techniques under an atmosphere of argon or nitrogen. All solvents used in the reactions were dried and deoxygenated by distillation under argon prior to use.

Routine NMR measurements were done on a Bruker WP 200 at an observation frequency of 200.133 MHZ for $^1$H: 50.323 MHZ for $^{13}$C: and 81.015 MHZ for $^{31}$P. Some high field $^1$H, $^{13}$C, $^{31}$P NMR data were obtained on a Varian RU400 NMR spectrometer at 399.052, 100.5777, 161.903MHZ, respectively. Key to NMR data: s, singlet; d, doublet; t, triplet; quart; quartet; quin, quintet; m, multiplet; br, broad; asterisk, pseudo.

EXAMPLE 1

The synthesis of Tris[p-(10-p-sulfonatophenyldecyl)phenyl]phosphine

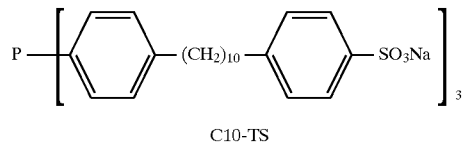

C10-TS 1-a. The synthesis of 10-bromo-1-phenyl-decane 1, 10-dibromodecane (100g, 0.33 mol) and diethylether (100 mL) were placed in a 500 ml three-neck flask equipped with a gas inlet, an equal-pressure dropping funnel and a reflux condenser. The solution was chilled with an ice-water bath. Phenyllithium (100 mL, 1.8 M, 0.18 mol in cyclohexane-ether) was added dropwise from the funnel and the addition was completed in 2 hours. The ice-water bath was removed and the reaction mixture was then heated to reflux for 36 hours to give a pale yellow solution that contained a white precipitate. The mixture was filtered and the solvent was removed under reduced pressure. The resulting yellow oil was then distilled under vacuum. 1,-bromo-1-phenyl-decane, 20.4 g, was recovered from the distillation at 148–152 C. (1 torr) as a colorless liquid (37% yield based on phenyllithium). $^1$H NMR ($\delta$ in CDCl$_3$): 1.28 (br.s., 10 H); 1.38 (m, 2H); 1.61 (*quin, $^3J_{H-H}$=7.0 Hz, 2H); 2.60 (t, $^3J_{H-H}$=7.7 Hz, 2H); 3.39 (t, $^3J_{H-H}$=6.9 Hz, 2H); 7.1–7.3 (m, 5H). $^{13}$C NMR ($\delta$ in CDCl$_3$): 28.15 (s, 1C); 28.73 (s, 1C); 29.27 (s, 1C); .29.39 (s, 1C); 29.43 (s, 2C); 31.46 (s, 1C); 32.83 (s, 1C); 33.94 (s, 1C); 35.95 (s, 1C); 125.54 (s, 1C); 128.19 (s, 2C); 128.37 (s, 2C); 142.87 (s, 1C). MS: 298 (M+).

1-b. The synthesis of 4-(10-phenyldecyl)-1-chlorobenzene 1-bromo-4-chlorolbenzene (14.0g, 0.073 mol) in 100 mL diethyl ether was introduced into a 250 ml three-neck flask equipped with an Ar inlet, two equal-pressure dropping funnels. The solution was chilled with ice-water bath. n-Butyllithium (46 ml, 1.6 M in hexanes) was added from the dropping funnel. The addition was completed in 15 min and immediately 10-bromo-1-phenyl-decane (20 g, 0.067 mol) in 20 ml diethyl ether was introduced in 10 min. The ice-water bath was then removed and the mixture was allowed to warm up to room temperature. The dropping funnel was replaced with a condenser and the reaction mixture was then set to reflux for 72 hours. The resulting yellow solution with white precipitate was filtered and the solvent was removed from the filtrate under reduced pressure. The product,4-(10-phenyldecyl)-1-chlorobenzene was purified by vacuum distillation in 26 % yield (5.7 g, colorless oil, bp: 190° to 195° C. at 1 torr.). $^1$H NMR ($\delta$ in CDCl$_3$): 1.27 (br.s., 6 H); 1.28 (br.s., 6 H); 1.57 (m, 4H); 2.57 (m, 4H); 7.0–7.3 (m, 9H). $^{13}$C NMR ($\delta$ in CDCl$_3$): 29.15 (s, 1C); 29–30 (s, 1C); 29.42 (s, 1C); 29.46 (s, 1C); 29.52 (s, 2C); 31.34 (s, 1C); 31.48 (s, 1C); 35.27 is (s, 1C); 35.97 (s, 1 C); 125.53 (s, 1C); 128.19 (s, 2C); 128.23 (s, 2C); 128.32 (s, 2C); 129,70 (s, 2C); 131.50 (s, 1C) 141.29 (s, 1C); 142.91 (s, 1C);. MS: 328 (M+).

1-c. The synthesis of Tris[p-(10-phenyldecyl)phenyl]phosphine 4-(10-phenyldecyl)-1-chlorobenzene (2.4 g, 7,3 mmol) in 50 ml diethylether/THF (50/50) was placed in a 100 ml side-armed flask under argon with an ice-water bath. Lithium (0.10 g, 14.6 mmol) was chopped directly into the flask. The solution was dark red in a few minutes. The ice-water bath was removed and the mixture was stirred for additional 4 hours. The resulting deep-red solution was filtered to remove LiCl. The solution was chilled with an ice-water bath and PCl$_3$, (0.33 g, 2.4 mmol) in 10 ml diethyl ether was added dropwise from an equal-pressure dropping funnel over a 15 minute period and the mixture was stirred overnight. A pale yellow solution with precipitate resulted. The solvents were removed under reduced pressure and replaced with 50 ml diethyl ether. The mixture was then filtered and the ether solution was further washed twice with 10 ml water and dried over MgSO$_4$. The ether was then removed and the final product, as a yellow oil at room temperature, was further purified by recrystallization with 50 ml pentane at −78° C. Tris[p-(10-phenyldecyl)phenyl] phosphine, a pale yellow oil, was recovered in 75% yield (1.64g). $^1$H NMR ($\delta$ in CDCl$_3$); 1.26 (br.s, 18 H); 1.29 (br.s., 18 H); 1.59 (m, 12H); 2.58 (*quart, 12H); 7.10–7.30 (m, 27H). $^{13}$C NMR ($\delta$ in CDCl$_3$); 29.33 (s, 3C); 29.37 (s, 3C); 29.48 (s, 3C); 29.50 (s, 3C); 29.55 (s, 3C); 29.56 (s, 3C); 31.32 (s, 3C); 31.53 (s, 3C); 35.79 (s. 3C); 35.99 (s, 3C); 125.53 (s, 3C); 128.20 (s, 6C); 128.38 (s, 6C); 128.53 (d, $^3J_{C-P}$=7.2 Hz. 6C); 133.63 (d, $^2J_{C-P}$=19.8 Hz, 6C); 134.38 (d. $^1J_{C-P}$=9.6 Hz, 3C); 142.93 (s, 3C); 143.49 (s, 3C). $^{11}$PNMR ($\delta$ in Cdcl$_3$); −7.1 (s). MS; 926 (M+as oxide).

1d. The synthesis of Tris[p-(10-p-sulfonatophenyldecyl)phenyl]phosphine-C10-TS

Tris[p-(10-phenyldecyl)phenyl]phosphine (1.6 g, 1.8 mmol), was dissolved in 8 ml H$_2$SO$_4$ (96%) with an ice-water bath. The brown solution was stirred at room temperature for 6 hours. The mixture was then neutralized by 20% (w/w) aqueous NaOH. The final pH was 8.5. 300 ml of methanol was added and the mixture was brought to reflux for 30 min. The precipitate, NaSO$_4$, was then filtered and the salt was washed with 100 ml hot methanol. Two portions of the solution were combined and the volume was reduced to 10 ml. 100 ml of acetone was then added to generate a white precipitate. The precipitate, Tris-(10-p-sulfonatophenyldecyl) phenyl]phosphine 1, was collected by filtration and dried under vacuum (1.75 g, 82% yield). $^1$H NMR ($\delta$ in CD$_3$OD): 1.27 (br.s, 18 H); 1.30 (bi.s., 18 H); 1.60 (m, 12H); 2.60 (m, 12H); 7.14 (br.*d, 12H); 7.22 (*d, 6H); 7.72 (*d, 6H). $^{13}$C NMR ($\delta$ in CD$_3$OD): 30.32 (s, 3C); 30.37 (s, 3C); 30.54 (s, 3C); 30.57 (s, 3C); 30.67 (s, 6C); 32.57 (s, 6C); 36.67 (s, 3C): 36.70 (s, 3C); 126.99 (s, 6C); 129.25 (s, 6C): 129.65 (d, $^3J_{C-P}$=6.8 Hz, 6C); 134.67 (d, $^2J^{C-P}$=19.8Hz, 6C), 135.82 (d, $^1J_{C-P}$=11.5 Hz, 3C); 143.72 (s, 3C); 144.89 (s, 3C); 146.64 (S, 3C). $^{31}$PNMR ($\delta$ in CD$_3$OD): −6.2 (s). MS: 1233 (M+1 as oxide).

EXAMPLE 2 (Comparative)

Synthesis of tetrasulfonated 2,2'-Bis{di[p-(10-phenyldecyl)phenylphosphinomethyl}-1,1'-biphenyl

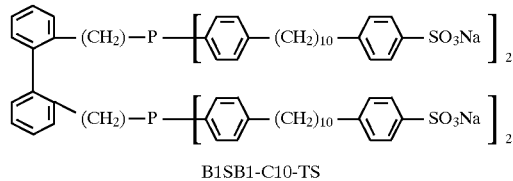

B1SB1-C10-TS 2-a. The synthesis of Di[p-(10-phenyldecyl)phenyl] chlorophosphine p-(10-phenyldecyl)phenyllithium (8.0 mmol), generated from the lithiation of 4-(10-phenyldecyl)-1-chlorobenzene (2.63 g, 8.0 mmol) in 50 ml solvent (Et$_2$O/THF 1/1) as described previously, was added dropwise to CH$_3$OPCl$_2$ (0.53 g, 4.0 mmol) in 15 ml solvent (Et$_2$O/THF 1/1) at −70° C. The addition was completed in 1 hour. The reaction mixture was stirred overnight at room temperature. The precipitate was filtered and the solvent of the solution was removed at reduced pressure. PCl$_3$ (9 ml) was added to the resulting viscous oil and stirred for 24 hours. Then the mixture was kept at 70° C. and 1 mm Hg for 2 hours to remove excess PCl$_3$ and byproduct. The product, di[p-(3-phenylpropyl)phenyl]chlorophosphine, was obtained as a pale yellow viscous oil in quantitative yield. $^{31}$PNMR($\delta$ in CDCl$_3$): 81.1 (s).

2-b. The synthesis of 2,2'-Bis{-di[p (10-phenyldecyl) phenyl]phosphinomethyl}-1,1'-biphenyl Di[p-(10-phenyldecyl)phenyl]chlorophosphine (2.55 g, 4.0 mmol) was dissolved in 60 ml THF and Li (0.056 g, 8.0 mmol) was chopped directly into the reaction flask under Ar. A deep red solution resulted in 10 minutes and all the lithium was consumed in 5 hours. The solution was then filtered and 2,2'-dibromomethyl-1, 1'-biphenyl (0.68 g, 2.0 mmol) in 20 ml THF was added dropwise with an ice-water bath. The color of the solution was slowly changed to pale yellow. The mixture was stirred for additional 10 hours before the solvent was removed by vacuum. 50 ml diethyl ether was added and it was washed with 3×20 ml H$_2$O. The ether phase was dried over MgSO$_4$ and the solvent was then removed by vacuum. The resulting pale yellow viscous oil was further purified by recrystallization with 50 ml pentane at 78° C. 1.5 g (54% yield) of2,2'-Bis {di[p-(10-phenyldecyl)phenyl]phosphinomethyl}-1,1'-biphenyl was recovered as a pale yellow oil. $^1$HNMR ($\delta$ CDCl$_3$): 1.26 (br.s, 24H); 1.29 (br.s, 24H); 1.59 (m, 16H); 2.53 (t, $^3J_{H-H}$=6.1 Hz, 8H); 2.59 (t, $^3J_{H-H}$=7.7 Hz, 8H); 3.12 (*quart, 4H); 6.9–7.4 (m, 44H). $^{13}$C NMR ($\delta$ in CDCl$_3$); 29.31 (s, 4C); 29.35 (s, 4C); 29.48 (br.s, 8C); 29.56 (br.s, 8C); 31.33 (d, $^1J_{C-P}$=7.6 Hz, 2C); 31.51 (br.s, 8C); 35.73 (s, 4C); 35.97 (s, 4C); 125.50 (s, 4C); 126.95 (s, 2C); 128.17 (s, 8C); 128.35 (s, 8C), 129.73 (d, $^3J_{C-P}$=10.0 Hz, 2C); 130.38 (s, 2C); 132.60 (d, $^3J_{C-P}$=19.1 Hz, 8C); 133.17 (d, $^2J_{C-P}$=19.8 Hz, 8C); 134.97 (d, $^1J_{C-P}$= 14.6 Hz, 4C); 135.31 (s, 2C); 135.96 (d, $^3J_{C-P}$=8.3 Hz, 2C); 140.86 (d, $^2J_{C-P}$=3.8 Hz, 2C); 142.88 (s, 4C): 143.10 (s, 4C). $^{31}$NMR ($\delta$ in CDCl$_3$); −14.1 (s). Mass Spectroscopy (FAB, on phosphine oxide): 1447 (M +1)

2-c. Synthesis of tetrasulfonated 2,2'-Bis{di[p-(10-phenyldecyl)phenyl]phosphinomethyl}-1,1'-biphenyl (B1SB1 -C10-TS)

2,2'-Bis{di[p-(10-phenyldecyl)phenylphosphinomethyl}-1,1'-biphenyl (1.3 g, 0.9 mmol), was dissolved in 8 ml H$_2$SO$_4$ (96%) with an ice-water bath. The brown solution was stirred at room temperature for 7 hours The mixture was then neutralized by 20% (w/w) aqueous NaOH. The final pH was 8.0. 300 ml of methanol was added and the mixture was brought to reflux for 30 min. The precipitate, $NaSO_4$, was then filtered and the salt was washed with 100 ml hot methanol. Two portions of the solution were combined and the volume was reduced to 10 ml. 70 ml of acetone was then added to generate a white precipitate. The precipitate, sulfonated 2,2'-bis {di[p-(10-phenyldecyl)phenyl]phosphinomethyl}-1,1'-biphenyl, was collected by filtration and dried under vacuum (1.1 g, 67% yield). 'HNMR ($\delta$ in $CD_3OD$); 1.30 (br, s, 48H); 1.59 (m, 16H); 2.55 (t, $^1J_{H-H}$= 6.7 Hz, 8H); 2.61 (t, $^3J_{H-H}$=8.2 Hz, 8H); 3.05 (*quart, 4H); 6.8–7.8 (m, 40H). $^{13}CNMR$ ($\delta$ in $CD_3OD$); 30.35 (br.s, 8C); 30.61 (br.s, 8C): 30.73 (br.s, 8C); 32.62 (br.s, 8C); 34.27 (d, $^1J_{C-P}$=13.3 Hz, 2C): 36.68 (br.s, 8C); 126.99 (s, 8C); 129.26 (br.s, 16C), 129.38 (s, 4C); 129.55 (s, 4C); 131.28 (s, 2C): 131.53 (s, 2C); 133.63 (d, $^3J_{C-P}$=18.3 Hz. 8C); 134.45 (d, $^2J_{C-P}$=19.8 Hz, 8C): 143.71 (s, 4C); 146.65 (s, 4C). $^{31}PNMR$ ($\delta$ in $CD_3OD$): –12.3(s). Mass Spectroscopy (FAB, in glycerol matrix) 1845 (M*+Na).

EXAMPLE 3(Comparative)

Using the procedure of Example 2, BISBI-$C_3$-TS was prepared using propyl instead of decyl.

Scheme 1 shows the preparation of a water-soluble aryl diphosphane ligand, 2,2'-Bis{di[p-(3-p-sulfonatophenylpropyl) phenyl]phosphinomethyl}-1,1'-biphenyl (BISBI-$C_3$-TS).

$C_3$—TS, $C_6$—TS and TPPTS was carried out in 30 ml stainless steel reaction vessel. The catalyst was made in-situ by mixing 0.76 ml 0.01 M Rh(acac) $(CO)_2$ in methanol and the required amount of 0.1 M aqueous solution of water-soluble ligand. Water was added to adjust the total aqueous methanol volume to 1.56 ml. The substrate, 0.60 ml of 1-octene, or 0.96 ml of 1-tetradecene, was then transferred into the reaction vessel under positive pressure of CO. Nonane, 0.40 ml, was added as an internal standard for gas chromatography analysis. Therefore, the volume of organic phase is 1.0 ml for 1-octene and 1.36 ml for 1-tetradecene. The Octene/Rh ratio was 500/1 in all catalytic runs. After the reaction vessel was loaded and pressurized with $CO/H_2$ to 210 psi, the reaction was initiated by placing the reaction vessel into a temperature bath preheated to 120° C. The temperature of the oil bath was controlled by an Omega CN 2000 temperature process controller. The reaction mixture was constantly stirred with a magnetic stir bar at 350 rpm. Catalytic reactions were terminated by removing the vessel from the oil bath and depressurizing when it had been cooled in an ice-water bath. In all cases the organic layer was colorless and readily separated from aqueous layer after the reaction.

The reaction product distribution was analyzed by gas chromatography on a Varian 3300 gas chromatograph equipped with a HP1 column 25m×0.32mm×0.52,$\mu$m and FID detector. He was the carrier gas; the temperature program was from 40° C. (4 min) to 220° C. (1 min) at a heating rate of 10 ° C./min.

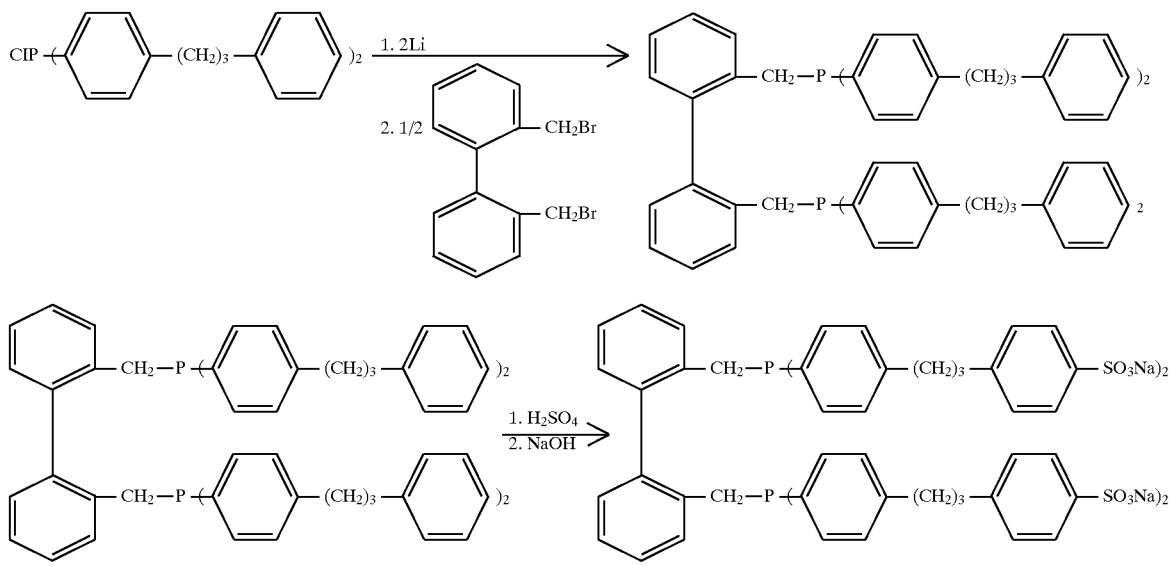

Scheme 1

EXAMPLE 4 (Comparative)

Preparation of $p[C_6H_4(CH_2)_3 C_6H_4$—p—$SO_3Na]_3$ ($C_3$—TS) and $p[C_6H_4(CH_2)_6C_6H_4$—p—$SO_3Na]_3(C_6$—TS)

$C_3$-TS and $C_6$-TS (sometimes referred to as $PC_3$—TS and $PC_6$—TS) were both prepared using the procedure outlined in Organometallics 1994, 13, 3761–3763.

Trisulfonated Triphenylphosphine (TPPTS) was commercially available.

EXAMPLE 5

Two-phase hydroformylatilon with rhodium catalyst of $C_{10}$—TS compared to $C_3$—TS, $C_6$—TS and TPPTS Two-phase hydroformylation of octene-1 with Tris[p-(1 0—p—sulfonatophenyldecyl)phenyl]phosphine ($C_{10}$—TS), The results are set forth in Table 1.

BRIEF DESRIPTION OF THE DRAWINGS

FIG. 1: Comparison of TPPTS, C3—TS, C6—TS for Octene Hydroformylation under Two Phase Reaction Conidtions.

TABLE 1

| L/Rh Ratio | TPPTS Yield of Nonanals (%) | TPPTS % of 1-Nonanal | C3-TS Yield of Nonanals (%) | C3-TS % of 1-Nonanal | C6-TS Yield of Nonanals (%) | C6-TS % of 1-Nonanal | C10-TS Yield of Nonanals (%) | C10-TS % of 1-Nonanal |
|---|---|---|---|---|---|---|---|---|
| 2 | 14 | 69 | 45 | 76 | 31 | 77 | 38 | 71 |
| 3 | 17 | 72 | | | | | 51 | 78 |
| 5 | 29 | 76 | | | | | 80 | 82 |
| 7 | 41 | 77 | | | | | 85 | 89 |
| 9 | 44 | 78 | | | | | 87 | 89 |
| 10 | 50 | 79 | 67 | 88 | 73 | 90 | | |

Reaction Conditions: reaction time, 1 hour; reaction temperature, 120° C.; initial pressure, 210 psi (at 25° C.); stirring rate is 350 rpm; [Rh] = 0.0049 M.

EXAMPLE 6

Hydroformylation of 1-tetradecene

The procedure of Example 5 was repeated using 1-tetradecene instead of 1-octene. The results are set forth in Table 2.

TABLE 2

Two Phase Hydroformylation of 1-tetradecene

| | TPPTS | PC3-TS | BISBI-C3-TS | PC10-TS | BISBI-C10-TS |
|---|---|---|---|---|---|
| yield (%) | 8.5 | 12 | 8.3 | 74* | 49 |
| % of 1-pentadecanal | 76 | 80 | 95 | 88 | 71 |

Reaction Conditions: reaction time, 20 hours; reaction temperature, 120° C.; initial pressure, 210 psi (at 25° C.), stirring rate is 350 rpm; [Rh] = 0.0049 M; L/Rh ratio = 7.
*including 11% of pentadecanols The quantitative conversion of substrates clearly proves the concept of surface active ligands, which allow catalytic reaction in a two-phase media with water-insoluble substrates. The unexpected yields when using C10—TS versus prior art catalysts was unusual and not expected.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof

What is claimed is:

1. A compound having the formula

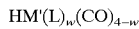

wherein M' is a transition metal, w is an integer which is 1–4, and L is a ligand having the formula

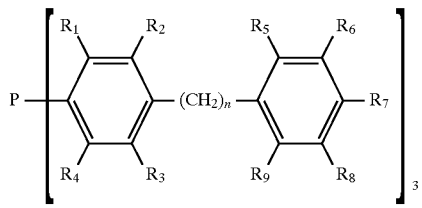

wherein $R_1$–$R_9$ are each independently selected from the group consisting of
(a) hydrogen,
(b) halogen,
(c) —$SO_3M$ where M is selected from the group consisting of alkali metal, alkaline earth metals, and $N(R)_4^{\ominus}$ where R is selected from the group consisting of H, alkyl $C_1$—$C_{20}$, and phenyl,
(d) alkyl $C_1$—$C_{20}$,
(e) —$CO_2M$ where M is the same as defined in (c),
(f) —$N^{\oplus}(R), X^{\ominus}$ where $X^{\ominus}$ is a halide and R is the same as defined in (c),
(g) —CN,
(h) —OR where R is the same as defined in (c),
(i) —C(O)—OR where R is the same as defined in (c), and
(j) —$P(R)_2$ where R is the same as defined in (c), and n is an integer which is 9, 10, or 11.

2. The compound as set forth in claim 1 wherein M is selected from the group consisting of Na, K, Li, Rb, Cs, Mg, Ca, and $NH_4$.

3. The compound as set forth in claim 1 wherein n is 9.

4. The compound as set forth in claim 1 wherein n is 10.

5. The compound as set forth in claim 1 wherein n is 11.

6. The compound as set forth in claim 1 wherein at least one of $R_1$–$R_9$ is —$SO_3M$.

* * * * *